United States Patent
Vetter et al.

(10) Patent No.: US 7,018,338 B2
(45) Date of Patent: Mar. 28, 2006

(54) METHOD AND DEVICE FOR PULSE RATE DETECTION

(75) Inventors: Rolf Vetter, Yverdon (CH); Philippe Renevey, Lausanne (CH); Roland Gentsch, Hauterive (CH); Jens Krauss, Neuchatel (CH); Yves Depeursinge, Servion (CH)

(73) Assignee: CSEM Centre Suisse d'Electronique et de Microtechnique SA, Neuchatel (CH)

( * ) Notice: Subject to any disclaimer, the term of this patent is extended or adjusted under 35 U.S.C. 154(b) by 74 days.

(21) Appl. No.: 10/255,068

(22) Filed: Sep. 26, 2002

(65) Prior Publication Data

US 2003/0065269 A1    Apr. 3, 2003

(30) Foreign Application Priority Data

Sep. 28, 2001 (EP) .................................. 01203686

(51) Int. Cl.
*A61B 5/02* (2006.01)
*A61B 6/00* (2006.01)

(52) U.S. Cl. ........................ 600/503; 600/500; 600/479

(58) Field of Classification Search ........ 600/500–504, 600/507, 473, 475, 476, 477, 479–481, 322–324
See application file for complete search history.

(56) References Cited

U.S. PATENT DOCUMENTS 5,025,791 A    6/1991  Niwa ........................ 128/670
5,055,671 A *  10/1991 Jones ..................... 250/227.21
6,002,952 A *  12/1999 Diab et al. .................. 600/310
6,018,673 A    1/2000  Chin et al. .................. 600/322
6,155,983 A *  12/2000 Kosuda et al. ............... 600/500
6,198,951 B1 *  3/2001  Kosuda et al. ............... 600/323
6,293,915 B1 *  9/2001  Amano et al. ............... 600/501
6,434,408 B1 *  8/2002  Heckel ....................... 600/336
2002/0188210 A1* 12/2002 Aizawa ....................... 600/503

FOREIGN PATENT DOCUMENTS

EP       0 645 117 A1      3/1995
EP       0 941 694 A1      9/1999

* cited by examiner

*Primary Examiner*—Navin Natnithithadha
(74) *Attorney, Agent, or Firm*—Steptoe & Johnson LLP

(57) ABSTRACT

Portable pulse rate detecting device for contact with human body tissue, including a light-emitting source for emitting radiant energy directed at through human body tissue; at least first and second light detectors for detecting intensity of radiant energy after propagation through human body tissue and for providing first and second input signals as a function of such propagation, a detecting device for providing a motion reference signal, and processing means for removing motion-related contributions from the first and second input signals and subtracting a calculated model based on the motion reference signal from each of the first and second input signals, wherein the processing means is also for removing measurement noise and residual non-modeled contributions from the first and second enhanced signals using a noise reduction algorithm.

23 Claims, 6 Drawing Sheets

METHOD AND DEVICE FOR PULSE RATE DETECTION

FIELD OF THE INVENTION

This invention is in the field of signal processing and is more specifically directed to pulse rate detection.

BACKGROUND OF THE INVENTION

Portable heart rate monitoring devices are classically composed of a processing device and an external probe (e.g. electronic stethoscope, optical measure at ear lobe, chest belt for electrocardiogram—ECG-based measurement, etc.). The use of an external probe is often considered as a reduction of the user's comfort. ECG-based pulse rate detecting devices using external electrode probes are for instance disclosed in documents U.S. Pat. Nos. 4,108,166, 6,018,677, 6,149,602 and WO 00/51680.

Various pulse rate detection systems are known in the art. Pulse rate detection devices using pressure sensitive transducers such as piezoelectric elements are for instance disclosed in documents U.S. Pat. Nos. 3,838,684, 4,195,642, 4,331,154, 5,807,267 and WO 80/00912.

More recently, measuring techniques based on so-called photoplethysmography (or PPG) have been proposed. PPG is an electro-optic technique of measuring the cardiovascular pulse wave found throughout the human body. This pulse wave is caused by the periodic pulsations of arterial blood volume and is measured by the changing optical absorption of radiant energy which this induces. The measurement system classically consists of a source of radiant energy (usually an infra-red light source), at least one detector for detecting the intensity of the radiant energy after propagation through the human body tissue and a data processing means for extracting bodily parameters such as pulse rate or oxygen concentration in the blood. Infra-red light is predominantly used since it is relatively well absorbed in blood and weakly absorbed in body tissue. Blood volume changes are therefore observed with a reasonable contrast. The principal advantage of PPG measurement resides in the fact that it is entirely non-invasive and can be applied to any blood bearing tissue, typically a finger, nail, ear lobe, nose and, in some instances, wrist.

Since light is highly scattered in tissue, a detector positioned on the surface of the skin can measure reflections (or transmissions) from a range of depths and those reflections (or transmissions) are variously absorbed depending on whether the light encounters weakly or highly absorbing tissue. Any change in blood volume will be registered by the detector at the surface since increasing (or decreasing) volume will cause more (or less) absorption. The effect will be averaged over many arteries and veins. In the absence of any blood volume changes, the signal level will be determined by the tissue type, skin type, probe positioning, static blood volume content and of course the geometry and sensitivity of the sensor itself.

PPG systems differentiate between light absorption due to blood volume and that of other fluid and tissue constituents by observation that arterial blood flow pulsates while tissue absorption remains static. As the illuminated blood flow pulsates, it alters the optical path length and therefore modulates the light absorption throughout the cardiac cycle. Non-pulsating fluids and tissues do not modulate the light but have a fixed level of absorption (assuming there is no movement).

The result of this absorption is that any light reflected from (or transmitted through) the pulsating vascular bed contains an AC component which is proportional to and synchronous with the patients plethysmographic signal. It is this modulated component which is known as the photoplethysmographic signal. This PPG signal is superimposed onto a DC level which represents the difference between incident radiant energy and the constant absorption of the tissue, blood and anything else in the optical path with constant absorption.

PPG measurement can be achieved by measurement of the intensity of radiant energy transmitted through (transmission mode systems) or reflected by (reflection mode systems) body tissue. A reflection mode system typically has much poorer signal to noise ratio, resulting from the fact that a smaller proportion of the light which is not absorbed will be reflected than transmitted. That is the reason why most of the prior art devices and systems use a detecting arrangement that is placed on the user's finger, nail, ear lobe, nose or part of the body through which light can easily be transmitted.

PPG has widely been used for measuring arterial oxygen saturation known as pulse oximetry. The technique relies on the knowledge that haemoglobin and oxyhaemoglobin absorb light to varying degrees as a function of wavelength. In particular, the absorption characteristics of red and near infrared light are inverted for the two species. It is thus possible to derive the proportion of oxyhaemoglobin and therefore the arterial oxygen saturation from a knowledge of the absorption characteristics of the arterial blood at these two wavelengths. PPG-based oximetry sensing devices employing sensors which are typically in contact with the user's finger or nail are for instance disclosed in documents U.S. Pat. No. 5,237,994, U.S. Pat. No. 5,645,060, U.S. Pat. No. 5,662,106, U.S. Pat. No. 5,934,277, U.S. Pat. No. 6,018,673, WO 99/52420, WO 99/62399 and WO 01/25802. PPG-based oximetry and heart rate detecting devices intended to be worn on or around other parts of the human body such as the wrist or ear, are also known, for instance from documents U.S. Pat. No. 5,807,267 and WO 97/14357.

One of the main problems of PPG measurement is corruption of the useful signal by ambient light and other electromagnetic radiations (so-called light artefacts) and by voluntary or involuntary subject movement (so-called motion artefacts). These artefacts lead to erroneous interpretation of PPG signals and degrade the accuracy and reliability of PPG-based algorithms for the estimation of cardiovascular parameters.

Processing of ambient light artefacts is not critical because the influence of ambient light can be measured using multiplexing techniques and the PPG signal can be restored using subtractive-type techniques. Reference can here be made to the article "Effect of motion, ambient light, and hypoperfusion on pulse oximeter function", Trivedi N. et al., Journal of Clinical Anaesthesia, vol 9, pp. 179–183, 1997, for a description of these problems. In contrast, processing of motion artefacts is a tough task since its contribution often exceed that of the useful pulse-related signal by an order of magnitude. It is essentially caused by mechanical forces that induces changes in the optical coupling and the optical properties of the tissue. Motion artefacts are a particularly critical problem for the design of a wrist-located pulse detecting device.

Several methods have been proposed to reduce motion artefacts in PPG signals. Feature-based algorithms have been proposed to discard the corrupted segments from the signals for instance in document WO 94/22360 (corresponding to U.S. Pat. No. 5,368,026). This kind of approach allows one to reduce the occurrence of false alarms in clinical environments, but it often degrades the signals with small motion artefacts contributions. This could lead to erroneous estimation of cardiovascular parameters.

In order to circumvent this drawback, model-based noise cancelling techniques have been applied more recently for the enhancement of optical signals. Examples are for instance described in documents U.S. Pat. No. 5,490,505, WO 94/03102 and in articles "Simple photon diffusion analysis of the effects of multiple scattering on pulse oximetry", Schmitt J., IEEE Transactions on Biomedical Engineering, vol. 38, pp. 1194–2002, December 1991, and "Noise-resistant oximetry using a synthetic reference signal", Coetzee F. M. et al., IEEE Transactions on Biomedical Engineering, vol. 47, pp. 1018–1026, August 2000. In such approaches a reference signal of motion is recorded and a parametric model is used subsequently to retrieve motion related influences in the optical signals. Nevertheless, motion references are classically obtained by piezo-sensors or optical measures and convey therefore only incomplete or local information of motion. This degrades the performance of model-based noise cancelling techniques since they require complete and low-noise motion reference signals.

SUMMARY OF THE INVENTION

It is thus a principal object of the present invention to provide a device and method for accurately monitoring and detecting heart rate based on photoplethysmography, even under intense physical activity.

More particularly, an object of the present invention is to provide a solution that allows for adequate removal of ambient light and motion contributions in the optical signals.

Another object of the invention is to provide a solution that is suitable for enabling measurement and detection to happen at the wrist level.

Accordingly there is provided a portable pulse rate detecting device the features of which are recited in aspect 1.

There is also provided a method for detecting pulse rate the features of which are recited in aspect 17.

Other advantageous embodiments of the invention are the object of the dependent aspect.

According to the present invention, an accurate motion detecting device is used to provide a reliable motion reference signal. This motion detecting device is preferably a fully integrated three dimensional accelerometer which exhibits a high accuracy and very low noise.

In order to achieve efficient removal of motion related artefacts in the optical signals, nonlinear model-based techniques are applied. This nonlinear modelling preferably consists in a polynomial expansion model using a moving average and an associated model selection based on the Minimum Description Length (MDL) criterion.

Furthermore, in order to grasp the spatial diversity of the optical characteristics of the tissue, at least two optical sensors are used. This two-channel arrangement, associated with an adequate noise reduction algorithm (preferably an algorithm based on so-called spatio-temporal Principal Component Analysis or PCA), allows one to remove measurement noise and non-modelled stochastic signal contributions as well as reduce artefacts related to finger movements which are generally not recorded by the accelerometer and therefore not initially cancelled.

Eventually, the heart rate is estimated from the enhanced signals using inter-beat extraction based on physiological properties of cardiac cells and maximum likelihood histogram clustering of the resulting time series.

An assessment of the performance of the proposed solution according to the invention has shown its high robustness and accuracy. It has to be pointed out that the application of nonlinear instead of linear modelling decreases the standard deviation of the detected heart rate of about one to two percent. This is mainly due to the inclusion of the parsimonious MDL-based model selection, which avoids an overfitting of the time series. Indeed, the full nonlinear model would retain pulse related components in the estimate of the motion artefacts. Since these components are subtracted from the optical signals, the quality of the enhanced signal and consequently the reliability of the estimated pulse are reduced. In contrast, MDL selects only movement related parameters in the model, which yields higher enhancement performance and a more accurate pulse estimation in adverse noisy environments.

BRIEF DESCRIPTION OF THE DRAWINGS

Other aspects, features and advantages of the present invention will be apparent upon reading the following detailed description of non-limiting examples and embodiments made with reference to the accompanying drawings, in which.

DESCRIPTION OF THE PREFERRED EMBODIMENT

Figure 1:
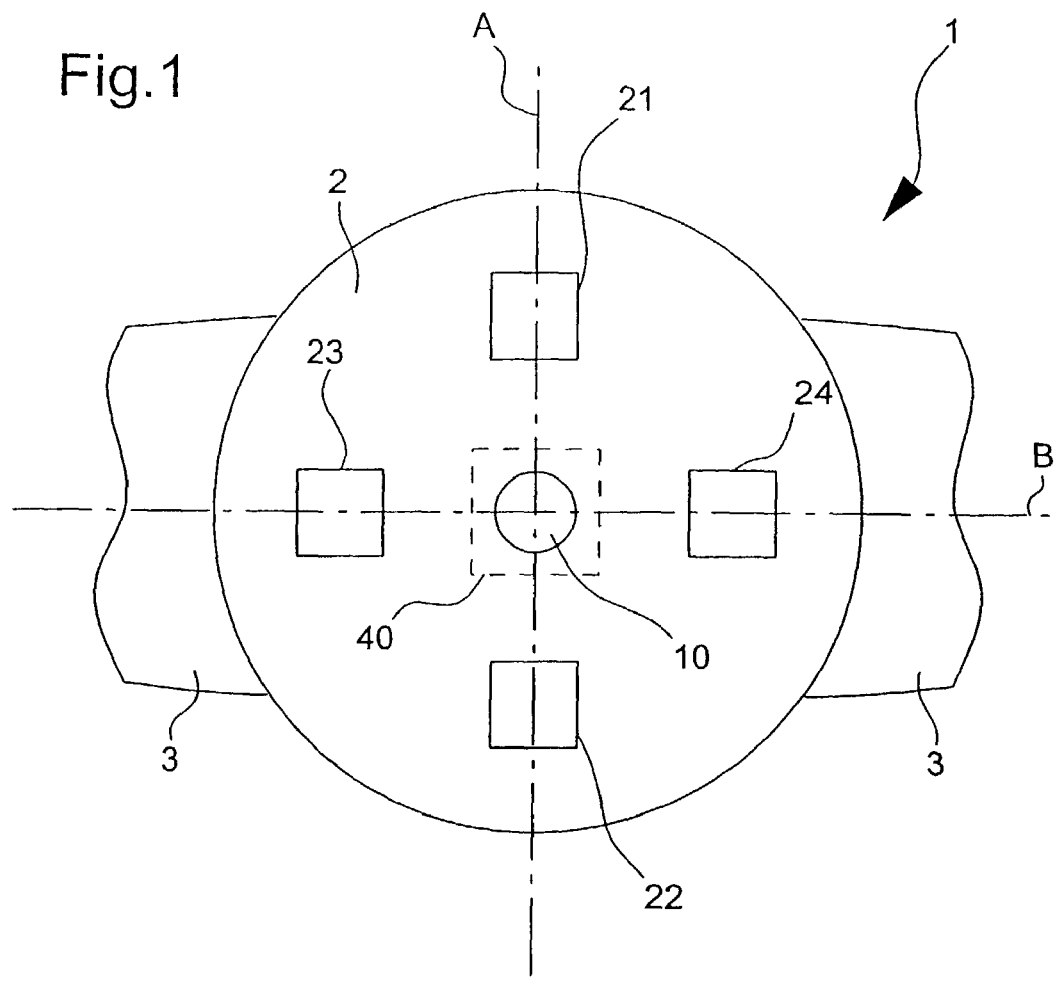
FIG. 1 is a schematic view of the bottom side (intended to come into contact with the body tissue) of a portable pulse rate detecting device according to the invention which is adapted to be worn on the wrist and comprising a light source and two pairs of light detectors arranged at the bottom side.
Figure 2:
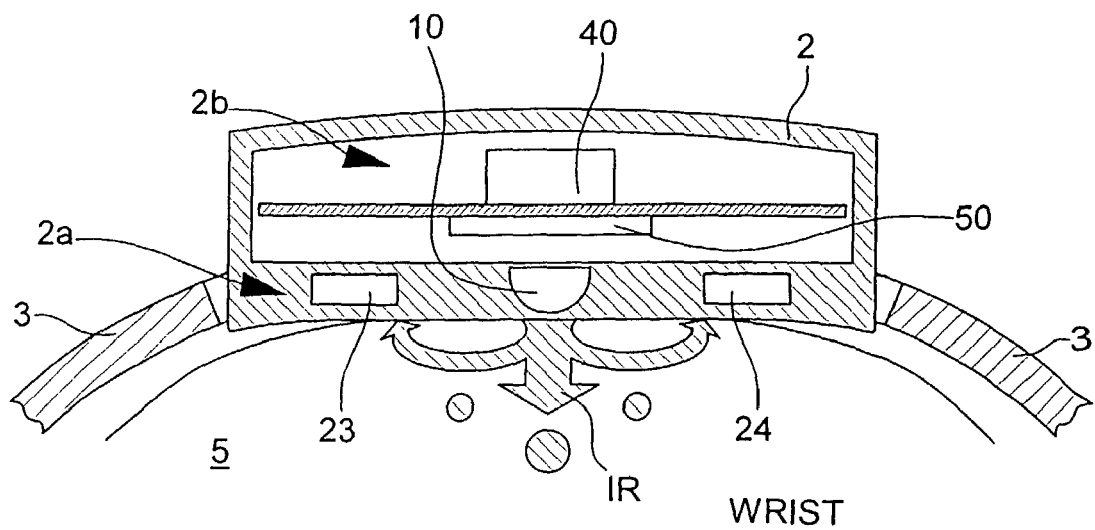
FIG. 2 is a schematic side view of the device of FIG. 1 further illustrating the arrangement of the accelerometer.

FIGS. 1 and 2 schematically show a top view of the bottom side and a side view of a wrist-located pulse rate detecting device, indicated globally by reference numeral 1, according to a preferred embodiment of the present invention.

While the invention will be described hereinbelow with respect to a portable device which is adapted to be worn on the wrist and which is based on the measurement of light reflected in the body tissue, it will be appreciated that the detecting device according to the present invention could be designed to be worn on other parts of the human body such as a patient's finger, nail, ear lobe or any other suitable member or part of the human body. In addition, the same principles could be applied to a detecting device based on the measurement of light transmitted through the body tissue (such as those typically used in pulse oximetry) where the signal to noise ratio is higher. In addition, these principles could be applied for pulse oximetry on the red and IR signals.

As shown in FIGS. 1 and 2, detecting device 1 comprises a housing 2 and a strap 3 for attaching detecting device 1 on the patient's wrist. Housing 2 comprises, located in a bottom side 2a of the device in contact with the skin, a light source 10 for emitting radiant energy at the surface of (or through) the human body tissue, designated by reference numeral 5. Light source 10 is preferably an infrared light emitting device (LED).

According to the preferred embodiment, housing 2 further includes two pairs of light detectors 21, 22 and 23, 24 for detecting the intensity of the radiant energy after propagation through the human body tissue. Such light detectors may conveniently be photodiodes. Preferably, the pairs 21, 22 and 23, 24 of light detectors are respectively disposed along first and second axes, indicated by references A and B, which are substantially perpendicular and parallel to the longitudinal axis of the strap, respectively. More specifically, light source 10 is located in a substantially central part of bottom side 2a and light detectors 21 to 24 are disposed around and at a determined distance from light source 10. In this example, this distance is advantageously selected to be approximately equal to 10 mm.

According to the invention, it will be appreciated that at least two light detectors are required for a proper detection of the heart rate. The detecting device of FIGS. 1 and 2 could thus be designed to have only one pair, three or even more than four light detectors. The number and spatial arrangement of these light detectors should however be selected in an adequate manner to provide sufficient spatial diversity for removing light-related artefacts and, as this will be seen hereinafter, to remove other contributions which cannot be detected by the accelerometer, such as reciprocal contributions due to finger movements. In that regard, the two-axes arrangement illustrated in FIGS. 1 and 2 has the advantage of allowing a good detection of such finger-related reciprocal contributions.

Referring again to FIGS. 1 and 2, housing 2 further comprises a motion detecting device 40 which is for example disposed in an upper part 2b of housing 2. This motion detecting device 40 is preferably a three dimensional accelerometer, that is, in effect, three accelerometers disposed along three orthogonal measurement axes and providing three dimensional acceleration data representative of the acceleration to which the device is subjected. This accelerometer is preferably and advantageously an accelerometer of the type manufactured by the company Colibrys S. A. under reference MS 6100. It will however be appreciated that other types of accelerometers or motion detecting devices could be used provided they deliver a reliable measure of motion of the pulse rate detecting device on and with respect to the human body tissue.

Processing of the signals can either be done by an external processing unit linked to the portable device (by means of a direct or wireless connection) or preferably by an adequately programmed digital signal processor or DSP (indicated schematically by reference numeral 50 in FIG. 2) housed within the device.

Optionally, the portable pulse rate detecting device according to the invention may further comprise means for outputting an indication of the detected pulse rate in the form of an optical, audible signal, or other sensorial signal. Such means could be a display, a buzzer, a vibrating device or any other suitable device adapted for transmitting information representative of the pulse rate measurement to the user. Additionally, the detecting device may also comprise alarm means for generating an alarm when the detected pulse rate reaches a determined threshold, which could be either a low or high threshold or both.

The basic principle of the invention resides in emitting an optical infrared (IR) signal at the surface of the human body tissue (or alternatively through the body tissue). This signal is then propagated through the tissue where it is submitted to modifications due to reflection, refraction, scattering and absorption. The resulting signal, after propagation through the tissue is grasped by the light detectors. Since variations of optical tissue characteristics are related to variations in the subcutaneous blood flow, the received signal can be used for the estimation of the heart rate.

When light is transmitted through biological tissue, several mechanisms are involved in the interaction between the light and the tissue. These interactions are reflection, refraction, scattering and absorption. Reflection and refraction occur at the interfaces between the probe and the subject. Scattering is due to the microscopic variations of the dielectric properties of the tissue. These variations are due to the cell membranes and the sub-cellular components (e.g. mitochondria and nuclei). For infra-red light, the absorption is mainly due to chromophores such as haemoglobin, myoglobin, cytochrome, melanin, lipid, bilirubin, and water. The relative importance depends on the wavelength considered and their distribution in the tissue.

Under ideal steady-state condition, the received IR light signal contains both a constant (DC) and a time varying (AC) component. The constant component is generally ascribed to baseline absorption of blood and soft tissue, non expansive tissue such as bone, as well as reflectance loss. The time varying component reflects the modification of the effective path length due to the expansion of the tissues subject to the varying blood pressure.

For the near IR wavelength, the light propagation into the tissue is governed by scattering and absorption. The so-called Beer-Lambert equation is generally used to describe the phenomenon of light absorption in biological tissue:

$$I_o(t) = I_i(t) \cdot \exp\left(-\sum_{j=1}^{n} \varepsilon_{\lambda,j} c_j(t) d_j(t)\right) \quad (1)$$

where $I_i(t)$ and $I_o(t)$ are the input and output light intensity, $\lambda$ is the wavelength of light and $c_j(t)$, $d_j(t)$ and $\varepsilon_{\lambda,j}$ represent, respectively, the concentrations, the spanning path length and the absorption coefficient of the different components. For further information about this subject, reference can be made to the articles "Noise-resistant oximetry using a synthetic reference signal", Coetzee F. M. et al., IEEE Transactions on Biomedical Engineering, vol. 47, pp. 1018–1026, August 2000, and "A review of the optical properties of biological tissues", Cheong W. -F. et al., IEEE Journal of Quantum Electronic, vol. 26, pp. 2166–2185, 1990.

As briefly mentioned in the preamble part of the description, voluntary or involuntary movements corrupt the PPG signal and create motion-related artefacts. It is generally accepted that motion artefacts are mainly due to modification of the optical properties of the tissue (modification of blood pressure, modification of the optical path, etc.). These modifications affect the corresponding components of the Beer-Lambert equation. Therefore, in presence of motion artefacts, the received intensity can be rewritten in function of the major contributions $$I_o(t) = I_i(t) \cdot \gamma_{tissue} \cdot \gamma_{pulse}(t) \cdot \gamma_{gravity}(t) \cdot \gamma_{motion}(t) \quad (2)$$

where $\gamma_{tissue}$ is the static attenuation due to the tissue, $\gamma_{pulse}(t)$ is due to pulsatile absorption of the blood, $\gamma_{gravity}(t)$ is due to change of position and $\gamma_{motion}(t)$ is due to dynamic changes of the tissue induced by the movement of the arm (assuming the device is worn on the wrist). It is obvious that the different contributions become additive if one takes the logarithm of expression (2) above.

When the subject is static, only the contributions of $\gamma_{pulse}(t)$ changes with time and it is then straightforward to remove the other contributions using a high-pass filtering. When the subject is moving, however, the contribution of the gravity and the modification of the interface between the detecting device and the body tissue are varying with time and they have to be removed from the signals in order to allow an accurate estimation of the heart rate. The contributions of the gravity are at low frequency and can be removed quite easily by an adaptation of the gain. The contributions of the motion is difficult to remove, especially if it is in the same frequency band as the heart rate. Therefore techniques have to be developed in order to remove the motion artefacts to obtain an accurate estimation of the heart rate.

It has been shown above that IR-signals recorded at the wrist are mainly affected by perturbations, such as tissue modifications, motion and gravity related artefacts. The main issue resides in the estimation of the mean heart rate from short time recordings of IR-signals (e.g. 10 seconds). It is assumed that the tissue properties do not vary over the observed duration and for a dual channel approach, the log-corrected observed IR-signals ($y_1(t)$, $y_2(t)$) given by expression (2) can be written as $$y_1(t) = s_1(t) + n_{m1}(t) + n_1(t)$$

$$t = 0, \ldots, N_t - 1 \quad (3)$$

$$y_2(t) = s_2(t) + n_{m2}(t) + n_2(t)$$

where $s_1(t)$, $s_2(t)$ are pulse pressure related signal contributions, $n_{m1}(t)$, $n_{m2}(t)$ are artefacts due to motion and gravity, $n_1(t)$, $n_2(t)$ include measurement noise and non-modelled stochastic signal contributions and $N_t$ is the number of observed samples.

Figure 3:
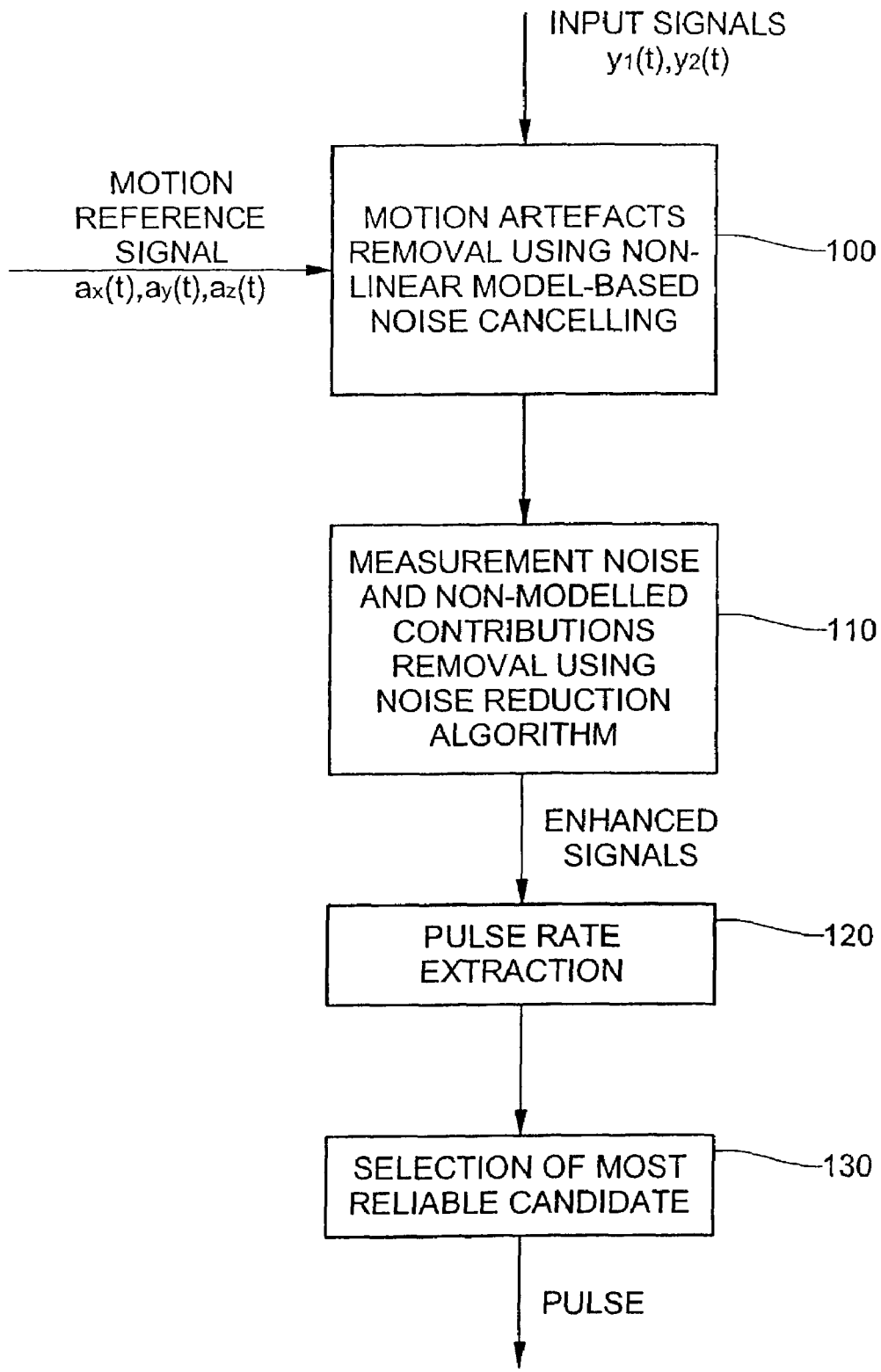
FIG. 3 is a flow chart of the preferred method for pulse rate detection according to the invention.

In order to obtain a robust pulse detection in a large variety of experimental conditions, namely non-stationary environments, the proposed method according to the present invention works on a frame-to-frame basis with a frame duration of e.g. 3 seconds and it consists of mainly a three step algorithm as shown in FIG. 3.

In a first step 100, the observed optical signals $y_1(t)$, $y_2(t)$ are enhanced using nonlinear, model-based noise cancelling techniques (see for instance "Adaptive Filter Theory", Haykin S., Prentice Hall, 1991). For this to be achieved, according to the present invention, an accurate motion reference signal (i.e. acceleration signals $a_x(t)$, $a_y(t)$ and $a_z(t)$) is provided by the accelerometer. The non-linear modelling essentially consists in a polynomial expansion model and an associated model selection based on the Minimum Description Length (MDL) criterion. Such techniques are already known as such by those skilled in the art. Reference can for instance be made to "Nonlinear Biomedical Signal Processing" Celka P. et al., vol. 2, IEEE Press, 2000, and to the PhD thesis of M. R. Vetter (co-inventor) entitled "Extraction of efficient and characteristic features of multidimensional time series", EPFL Lausanne (Switzerland) 1999, which are both incorporated herein by reference.

The use of the parsimonious MDL selection criterion avoids an overfitting of the time series and ensures in this way that no pulse pressure related signal contributions are cancelled.

In a second step 110, measurement noise and non-modelled stochastic signal contributions in the two recorded channels are preferably removed. This is achieved, according to the preferred embodiment of the present invention, by a noise reduction algorithm based on spatio-temporal Principal Component Analysis (PCA). For further information about this PCA algorithm, reference will be made to the article "Blind source separation in highly noisy environments", Vetter R. et al., in First International Workshop on Independent Component Analysis and Signal Separation" (ICA'99), Aussois (France), pp. 491–496, 1999, which is also incorporated herein by reference. This step is not as such compulsory since a pulse rate measurement could be derived from the input signals after removal of the motion-related contributions.

In addition to the removal of measurement noise and non-modelled signal contributions, spatio-temporal PCA allows one to reduce artefacts related to finger movements, which are generally not cancelled in step 100. Indeed, finger movements do not necessarily imply a global displacement of the forearm and are therefore not grasped by the accelerometer. Finger movements, often imply tiny, reciprocal tendon related displacement of the forearm tissue, which yields reciprocal artefact contributions in the two channels. Due to the reciprocity of these signal contributions, they can efficiently be cancelled by a spatio-temporal PCA.

In a third step 120, the pulse rate is extracted from the enhanced IR-signals. This extraction essentially consists of an inter-beat interval extraction achieved through a classical maximum detection procedure, preferably with inhibition of peak detection during the refractory period of cardiac cells. In addition, a maximum likelihood histogram clustering of the resulting inter-beat intervals is performed (cf. "Vector Quantization and Signal Compression", Gersho A. et al., Kluwer Academic Publishers, 1992).

Eventually, in a fourth step 130, the most reliable candidate can be selected. A robust and reliable estimate of the pulse rate can be obtained through a nonlinear mapping of the two candidate values in function of their reliability measures. This nonlinear mapping is advantageously achieved by Multiple Layer Perceptron (MLP), which has been trained on data of various experimental setups as described in "Neural Networks", Haykin S., Macmillan College Publishing Company Inc., 1994.

Figure 4:
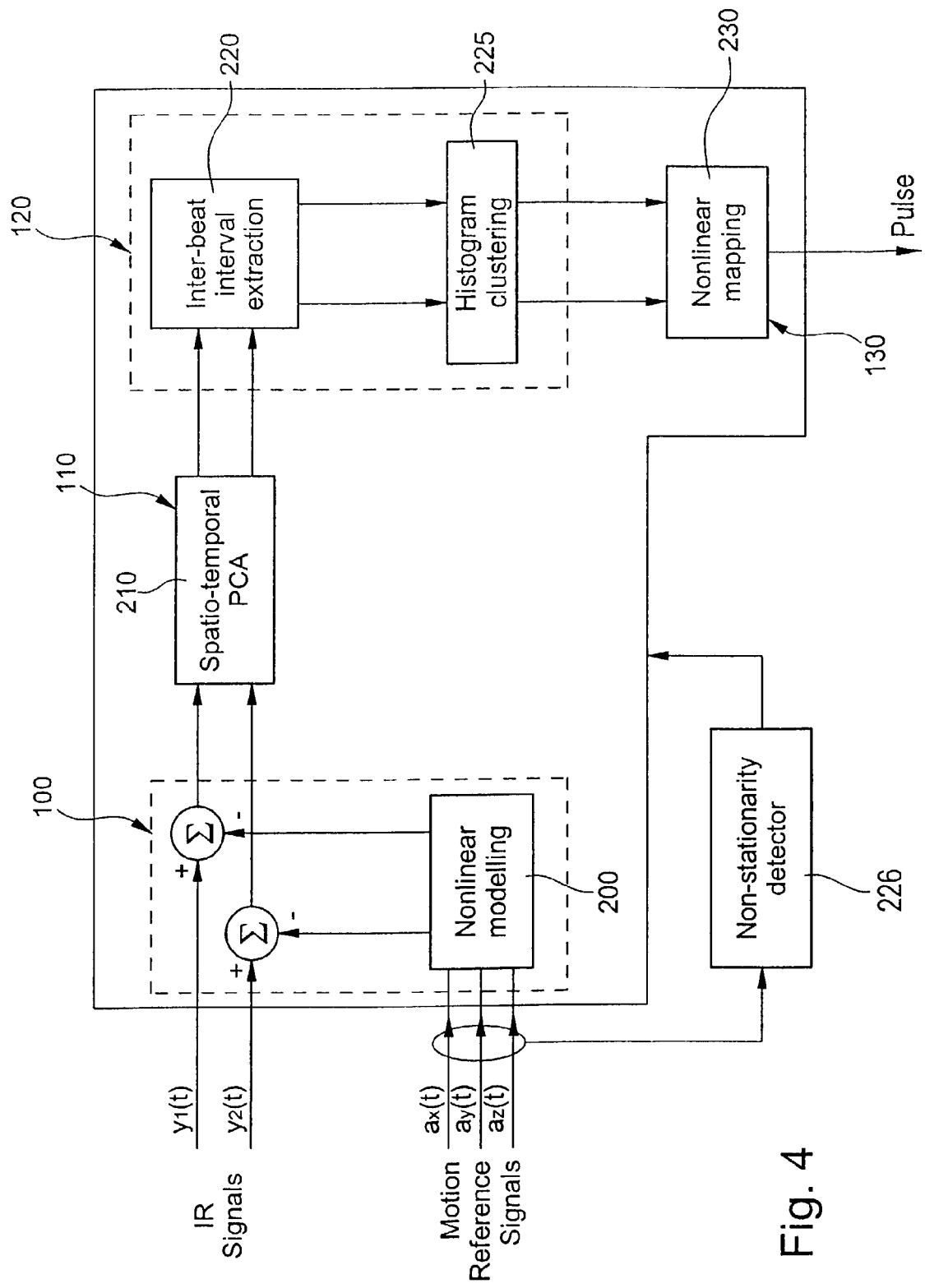
FIG. 4 is a block diagram illustrating a dual channel pulse detection algorithm according to the present invention which is based on nonlinear model-based motion artefact cancelling, coherence-based reduction of measurement noise and stochastic signal contributions, and a pulse detection using maximum likelihood histogram clustering.

A more detailed description of the preferred embodiment of the present invention will now be described in reference to the diagrams of FIG. 4 and FIGS. 5a to 5e. FIG. 4 shows a diagram illustrating the preferred algorithm according to the invention where block 200 refers to the nonlinear modelling based on the motion reference signal ($a_x(t)$, $a_y(t)$, $a_z(t)$), block 210 refers to the measurement noise and non-modelled contributions cancellation using PCA, block 220 refers to the inter-beat interval extraction on the two enhanced signals, block 225 refers to the maximum likelihood histogram clustering, block 226 refers to the detection of the non-stationary signal segments, and block 230 refers to the final selection of the most reliable candidate using a nonlinear mapping technique.

One of the key element in the proposed algorithm is the nonlinear model, which provides an estimation of the motion related contributions in the observed IR-signals (block 200 in FIG. 4). The relationship between time varying optical characteristics and its influence on IR-signals is globally described by the Beer-Lambert law hereinabove. Even though one can obtain linear characteristics of these variations of the optical characteristics by a logarithmic transformation, their relationship to a global motion reference signal, such as the one grasped by the accelerometers is complex and may be nonlinear. In order to take into account these potential nonlinear contributions, a third order polynomial moving average model NMA is preferably applied (such an NMA model is described in "Nonlinear Biomedical Signal Processing" to Celka P. et al., and "Extraction of efficient and characteristic features of multi-dimensional time series", to Vetter R. already mentioned hereinabove).

Moreover, since this model includes a parsimonious selection criterion (that is the MDL criterion) together with an efficient search algorithm, linear terms are first tested and nonlinear higher order polynomial terms are only included if they are required for an efficient and parsimonious description of the data at disposal. Thus, due to the efficiency of the MDL-based parameter selection, overfitting of the time series is avoided and high model-based noise reduction can be achieved.

Noise reduction based on PCA (block 210 in FIG. 4) has been shown to provide high enhancement performance in various applications (cf. "A signal subspace approach for speech enhancement", Ephraim Y. et al., IEEE Transactions on Speech and Audio Processing, vol. 3, pp. 251–266, 1995 and "Observer of autonomic cardiac outflow based on blind source separation of ECG parameters", Vetter R. et al., IEEE Transactions on Biomedical Engineering, vol. 47, pp. 578–582, 2000).

In order to take simultaneously advantage of the spatial and temporal correlations existing between and within the observed noisy signals, spatio-temporal PCA has been applied. The basic idea behind PCA-based noise reduction is to observe the noisy data in a large m-dimensional space of delayed coordinates. Since noise is assumed to be random, it extends approximately in a uniform manner in all directions of this space. In contrast, the dynamics of the deterministic system underlying the data confine the trajectories of the useful signal to a lower-dimensional subspace of dimension p<m. As a consequence, the eigenspace of the noisy mixtures is partitioned into a noise subspace and a signal-plus-noise subspace. Enhancement (i.e. noise reduction) is performed by projecting the noisy mixtures onto the signal-plus-noise subspace.

The main problem in PCA-based noise reduction algorithms is the optimal choice of the parameters p and m. For the selection of the optimal PCA dimension m, one can benefit from the fact that, in the given biomedical application, one deals with signals containing quasi-periodic contributions. The embedding dimension can therefore be estimated from the bandwidth of these quasi-periodic contributions. On the other hand, the choice of p is not critical in this application since we are looking mainly for one quasi-periodic contribution which is represented by p≈2.

Model-based noise reduction and artefact cancellation using spatio-temporal PCA described above are not able to cope with highly non-stationary signals such as the one resulting from random irregular movements. Indeed, irregular movement yield burst-like, non-stationary activity signals. Such signal segments constitute outliers from a statistical point of view and they induce large errors in the parameter estimation process. As a result, enhancement performance degrades drastically for random irregular movements.

In order to avoid this drawback, a method is thus preferably included for determining non-stationary signal segments in the motion reference signals $a_x(t)$, $a_y(t)$, $a_z(t)$ (block 226 in FIG. 4). Stationarity detection is achieved as follows:

firstly, an estimation of the variance of the activity signals $a_x(t)$, $a_y(t)$, $a_z(t)$ is performed on a frame-to-frame basis, with a length of overlapping successive frames of, e.g., 3 seconds;

secondly, the relative increment of variance of successive frames is computed;

thirdly, non-stationary segments are assessed for relative increments of variance larger than a determined threshold; and finally, signal enhancement and pulse detection are disabled during the detected non-stationary signal segments.

One can observe that this strategy provides pulse estimation only during stationary signal segments. However, since signal non-stationarity is caused by irregular random movement of short duration, missing probe values can be obtained through methods based on signal prediction. Furthermore, referring to the detecting device of the present invention, it will be appreciated that the light-emitting source (10 in FIG. 2), the light detectors (21 to 24 in FIG. 2) and/or the processing means (50 in FIG. 2) may be disabled when non-stationary signal segments are detected, this being also advantageous in terms of power consumption since processing of the signals is not unnecessarily performed in highly unstable environments. One can indeed obtain an efficient system with lowest power consumption.

Pulse detection through maximum likelihood histogram clustering (block 225 in FIG. 4) mentioned hereinabove, will now briefly be discussed. Estimation of the pulse rate is achieved on a frame-to-frame basis, with a frame duration of approximately 10 seconds (in the above illustrative example). Histogram clustering is performed as follows:

firstly, inter-beat intervals which are not physiologically plausible are discarded;

secondly, for each detected inter-beat interval IBI(n), one looks for all neighbouring inter-beat intervals closer than dIBI(n), where 0<d<1 determines the size of the neighbourhood;

thirdly, the centroid of the resulting cluster is evaluated and the number of inter-beat intervals of each cluster is determined to obtain the final histogram;

finally, the location of the maximum value of the histogram provides the mean heart rate and the ratio of the maximum value of the histogram with respect to the total number of detected intervals yields the reliability measure.

FIGS. 5a to 5d are diagrams respectively illustrating the evolution, as a function of time, (a) of the two optical signals $y_1(t)$, $y_2(t)$ provided by the light detectors, (b) of the measured acceleration signals $a_x(t)$, $a_y(t)$, $a_z(t)$ along the three orthogonal measurement axes, (c) of the two enhanced optical signals after removal of the motion artefacts, and (d) of the two enhanced optical signals after measurement noise removal (using PCA). FIG. 5e illustrates the corresponding electrocardiogram ECG.

Figure 5A:
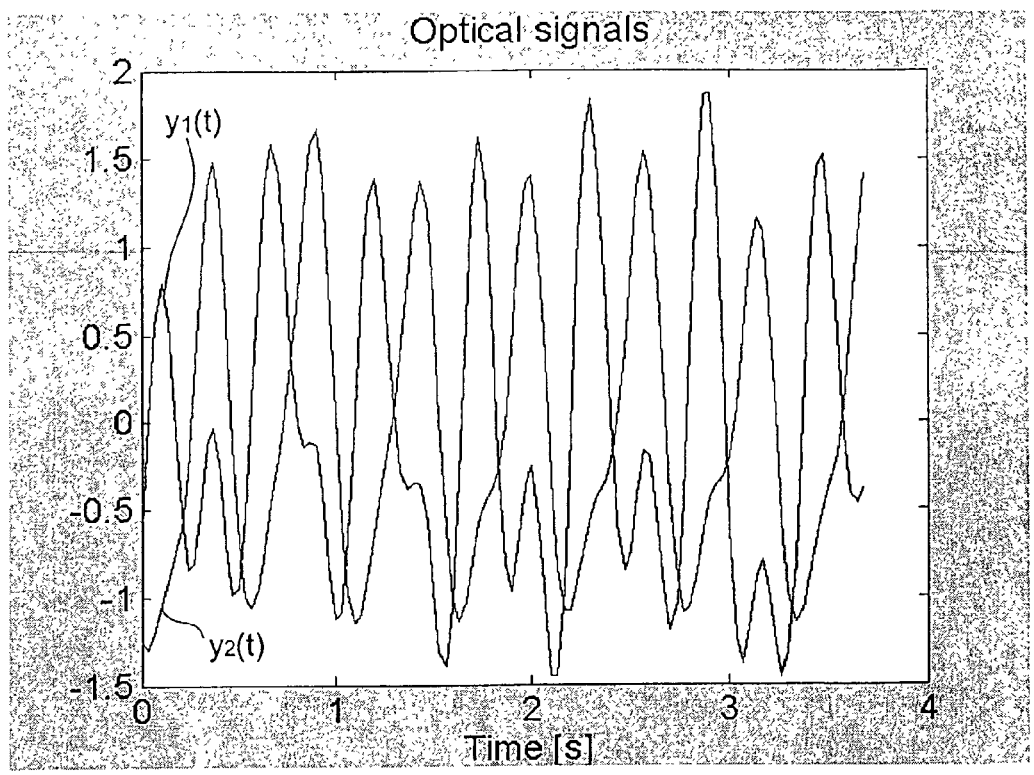
FIGS. 5*a* to 5*e* are diagrams respectively illustrating the evolution, as a function of time, (a) of optical signals provided by two light detectors, (b) of acceleration signals detected by the accelerometer along three measurement axes, (c) of the two optical signals after removal of the motion artefacts, (d) of the two optical signals after measurement noise removal (using PCA) and (e) a corresponding ECG electrocardiogram.
Figure 5B:
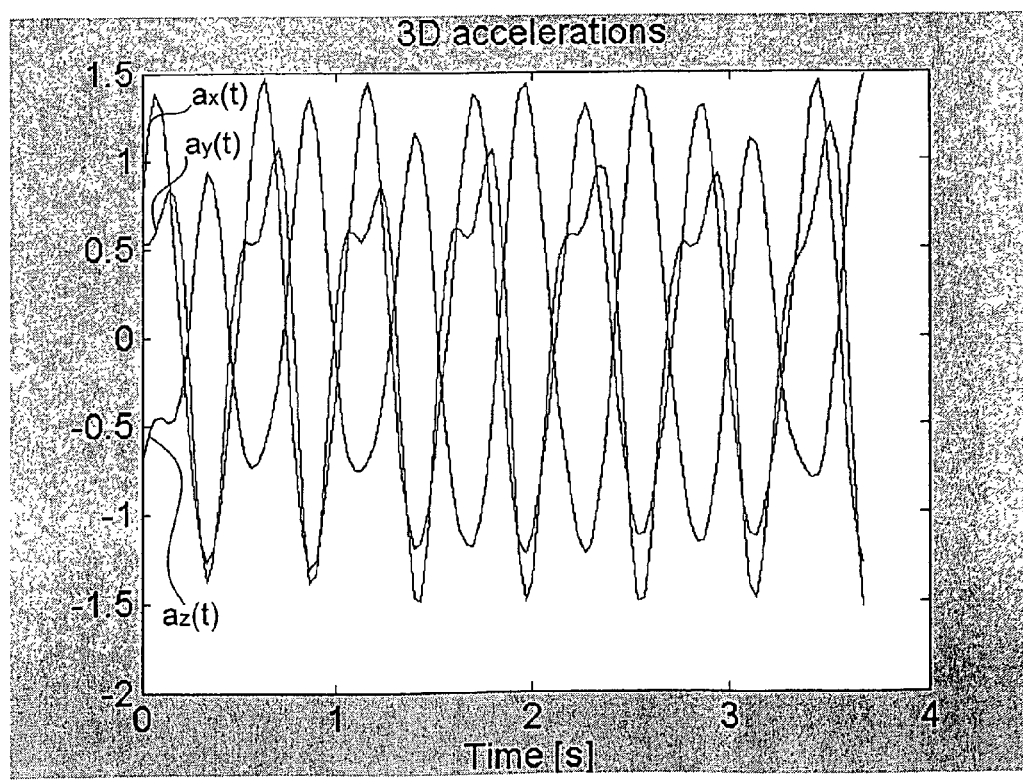
Figure 5C:
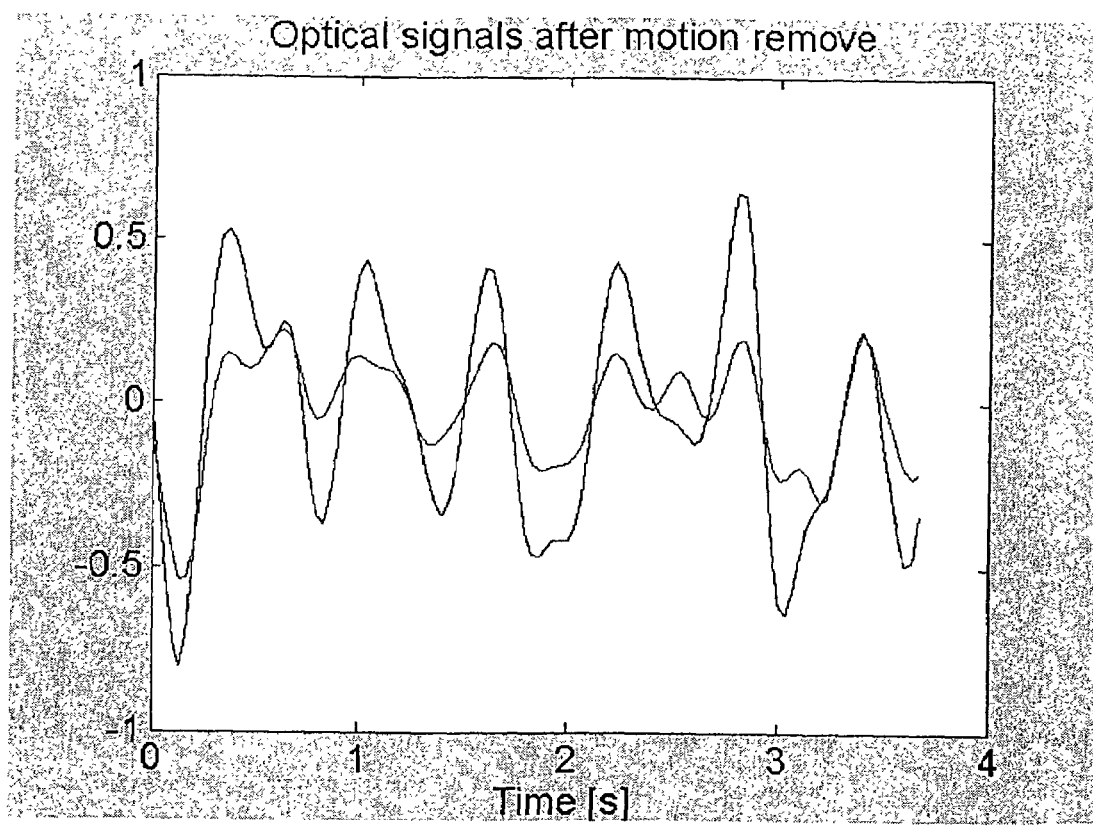

For the purpose of illustration, FIGS. 5a and 5b respectively show an example of two PPG optical signals $y_1(t)$, $y_2(t)$ and associated motion reference signals, i.e. acceleration signals $a_x(t)$, $a_y(t)$ and $a_z(t)$ provided by the three dimensional accelerometer. FIG. 5c shows the resulting optical signals after modelling and removal of the motion-related artefact, that is after subtraction of the constructed nonlinear models from both PPG optical signals $y_1(t)$, $y_2(t)$. After model-based artefact cancelling, one can see, in a qualitative manner, that pulse-related peaks are recovered, while motion-related contributions are discarded.

Figure 5D:
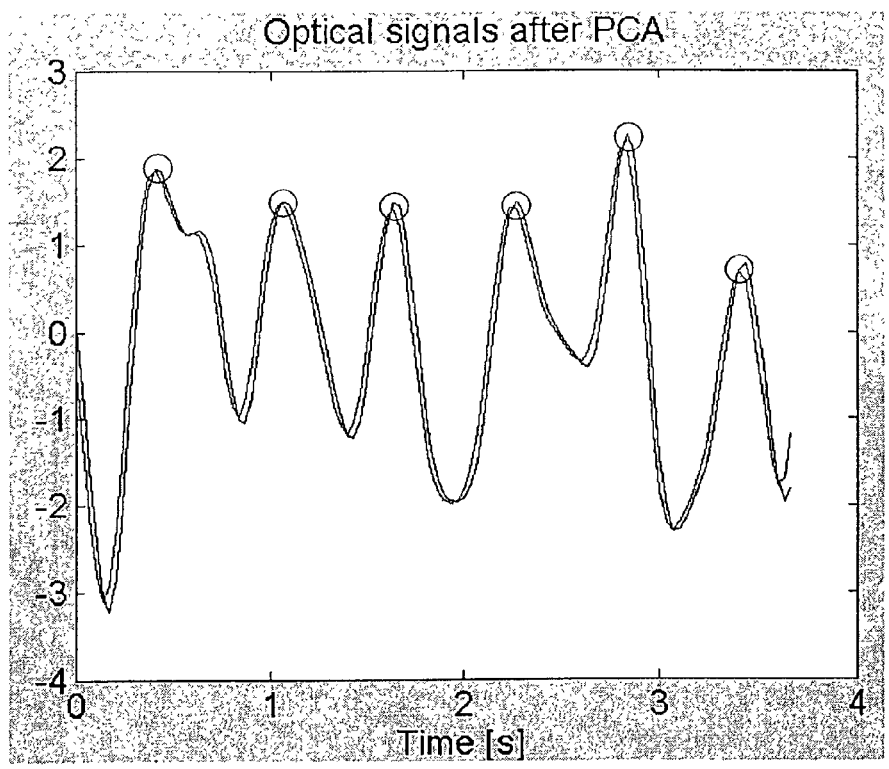
Figure 5E:
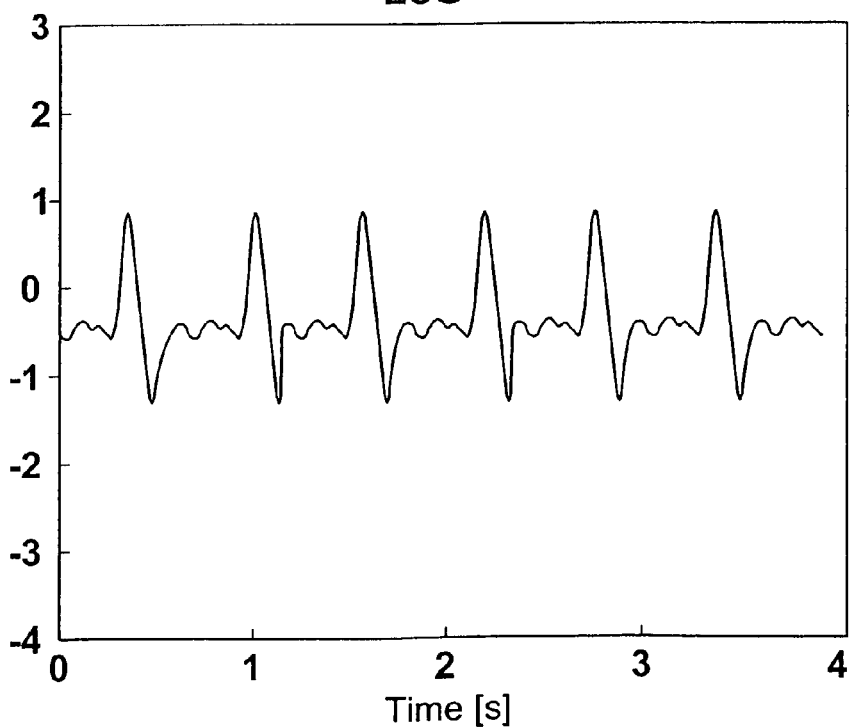

FIG. 5d shows the enhanced optical signals after noise reduction using PCA. Residual noise contributions due to tiny local movements not grasped by the accelerometers, modelling errors, and other stochastic influences are removed by spatio-temporal PCA. FIG. 5d also shows an almost perfect matching of the two enhanced optical signals, highlighting the efficiency of the proposed algorithm.

A thorough analysis of the signals of FIG. 5d with regard to the corresponding recorded ECG highlights that the information of inter-beat intervals (schematised by the detected signal peaks indicated by small circles in the Figure) is recovered up to a delay, which can be associated to the applied signal processing techniques.

Having described the invention with regard to certain specific embodiments, it is to be understood that these embodiments are not meant as limitations of the invention. Indeed, various modifications and/or adaptations may become apparent to those skilled in the art without departing from the scope of the annexed aspect. For instance, the invention shall not be meant to be applied only to pulse rate determination at the wrist level. The same principles could be applied with a device adapted to be worn on the user's finger, nail, ear lobe or other adequate part of the human body.

In addition, the present invention could also be modified to allow measurement of the oxygen saturation in the blood, provided that the device is equipped with separate red and infrared light sources. The above-described enhancing schemes would then be applied for both red and IR signals.

The proposed algorithm for pulse detection which has been presented hereinabove uses a frame-to-frame signal processing approach. Nevertheless, it has to be pointed out that all the above methods can be implemented in an adaptive form (see "Adaptive Filter Theory", Haykin S., Prentice Hall, 1991). The advantage of the proposed implementation resides mainly in a much lower computational load, which is a key element in the design of a portable unit.

Finally, as already mentioned hereinabove, the detecting device of the invention could be designed as a device adapted to fit around the user's ear, the light source and light detectors being conveniently disposed to emit and detect propagation of light through the ear lobe. An example of such a device is disclosed in document WO 97/14357 which has already been cited in the preamble part of the description. Such an ear-mounted device could be provided with means for generating an audible signal indicative of the detected pulse rate or of an alarm when a determined threshold is reached.

What is claimed is:

1. Portable pulse rate detecting device for contact with human body tissue, comprising:
   a light-emitting source for emitting radiant energy through human body tissue;
   at least first and second light detectors for detecting intensity of radiant energy after propagation through human body tissue and for providing first and second input signals ($y_1(t)$, $y_2(t)$) as a function of such detected radiant energy;
   a device for measuring motion of the detecting device with respect to human body tissue and for providing a motion reference signal ($a_x(t)$, $a_y(t)$, $a_z(t)$) as a function of said motion;
   processing means for removing, from said first and second input signals ($y_1(t)$, $y_2(t)$), motion-related contributions due to movement of the detecting device with respect to human body tissue and producing first and second enhanced signals,
   said processing means being arranged to calculate a model of said motion-related contributions based on said motion reference signal ($a_x(t)$, $a_y(t)$, $a_z(t)$) and to subtract this model from each of said first and second input signals ($y_1(t)$, $y_2(t)$),
   wherein said processing means is also for removing measurement noise and residual non-modelled contributions from said first and second enhanced signals using a noise reduction algorithm; and
   means for detecting non-stationary signal segments in said motion reference signal ($a_x(t)$, $a_y(t)$, $a_z(t)$) and for disabling at least one of said light-emitting source, said light detectors and said processing means when non-stationary signal segments are detected.

2. Portable pulse rate detecting device according to claim 1, wherein said model is a nonlinear model.

3. Portable pulse rate detecting device according to claim 2, wherein the model is selected using a Minimum Description Length (MDL) criterion.

4. Portable pulse rate detecting device according to claim 2, wherein said nonlinear model is a third order polynomial moving average model.

5. Portable pulse rate detecting device according to claim 1, wherein said noise reduction algorithm is based on Principal Component Analysis (PCA).

6. Portable pulse rate detecting device according to claim 1, wherein said processing means is for detecting peaks in said first and second enhanced signals and for extracting inter-beat intervals from said detected peaks to provide a pulse rate measurement, the detection of said peaks being inhibited during the refractory period of cardiac cells.

7. Portable pulse rate detecting device according to claim 1, wherein said detecting device comprises a strap for being worn around a wrist, said light-emitting source and said light detectors being located on a bottom side of said detecting device in contact with human body tissue.

8. Portable pulse rate detecting device according to claim 1, wherein said processing means is a digital signal processor DSP housed within said detecting device.

9. Portable pulse rate detecting device according to claim 1, wherein said device for providing the motion reference signal ($a_x(t)$, $a_y(t)$, $a_z(t)$) is a three dimensional accelerometer.

10. Portable pulse rate detecting device according to claim 1, further comprising means for outputting at least one of (1) an indication of the detected pulse rate in the form of an optical, audible or other sensorial signal and (2) an alarm when the detected pulse rate reaches a determined threshold.

11. Portable pulse rate detecting device for contact with human body tissue, comprising:
   a light-emitting source for emitting radiant energy through human body tissue;
   at least first and second light detectors for detecting intensity of radiant energy after propagation through human body tissue and for providing first and second input signals ($y_1(t)$, $y_2(t)$) as a function such detected radiant energy;

a device for measuring motion of the detecting device with respect to human body tissue and for providing a motion reference signal ($a_x(t)$, $a_y(t)$, $a_z(t)$) representative of such measured motion;

processing means for removing, from said first and second input signals ($y_1(t)$, $y_2(t)$), motion-related contributions due to movement of the detecting device with respect to human body tissue and producing first and second enhanced signals, said processing means for calculating a model of said motion-related contributions based on said motion reference signal ($a_x(t)$, $a_y(t)$, $a_z(t)$) and for subtracting said model from each of said first and second input signals ($y_1(t)$, $y_2(t)$); and means for detecting non-stationary signal segments in said motion reference signal ($a_x(t)$, $a_y(t)$, $a_z(t)$) and for disabling at least one of said light-emitting source, said light detectors and said processing means when non-stationary signal segments are detected, wherein said first and second light detectors are located on each side of the light-emitting source along a first axis, said detecting device further comprising third and fourth light detectors located on each side of the light-emitting source along a second axis substantially perpendicular to the first axis.

12. Portable pulse rate detecting device according to claim 11, further comprising a strap, said strap having said detecting device attached thereto, wherein said first and second axes are respectively perpendicular and parallel to a longitudinal direction of said strap.

13. Portable pulse rate detecting device according to claim 11, wherein said light-emitting source is located in a substantially central area of a side of the detecting device for use adjacent human body tissue, and said light detectors are located around said light-emitting source.

14. Portable pulse rate detecting device according to claim 11, wherein a distance between said light-emitting source and said light detectors is approximately 10 mm.

15. Portable pulse rate detecting device according to claim 11, wherein said light-emitting source is an infrared light-emitting device and said light detectors are photodiodes.

16. Portable pulse rate detecting device according to claim 11, wherein said processing means is a digital signal processor DSP housed within said detecting device.

17. Portable pulse rate detecting device according to claim 11, wherein said device for providing the motion reference signal ($a_x(t)$, $a_y(t)$, $a_z(t)$) is a three dimensional accelerometer.

18. Portable pulse rate detecting device according to claim 11, further comprising means for outputting at least one of (1) an indication of the detected pulse rate in the form of an optical, audible or other sensorial signal and (2) an alarm when the detected pulse rate reaches a determined threshold.

19. Method for detecting a pulse rate comprising:
emitting radiant energy through human body tissue by means of a light-emitting source;

measuring the intensity of radiant energy after propagation through the human body tissue by means of at least first and second light detectors located at a determined distance from said light-emitting source and providing first and second input signals ($y_1(t)$, $y_2(t)$) as a function of such detected radiant energy;

measuring motion of the detecting device with respect to human body tissue during propagation of said radiant energy through human body tissue by means of a motion detecting device and providing a motion reference signal ($a_x(t)$, $a_y(t)$, $a_z(t)$) as a function of such motion;

processing said first and second input signals ($y_1(t)$, $y_2(t)$) to remove motion-related contributions due to motion of the detecting device with respect to human body tissue and producing first and second enhanced signals, said processing comprising calculating a model of said motion-related contributions based on said motion reference signal ($a_x(t)$, $a_y(t)$, $a_z(t)$) and subtracting this model from each of said first and second input signals ($y_1(t)$, $y_2(t)$);

extracting the pulse rate from said first and second enhanced signals, said extracting including detecting peaks in said first and second enhanced signals and extracting inter-beat intervals from said detected peaks to provide a pulse rate measurement, the detection of said peaks being inhibited during the refractory period of cardiac cells;

performing a maximum likelihood histogram clustering of said inter-beat intervals;

determining a reliability measure of the pulse rate measurement of each one of said first and second enhanced signals and performing a nonlinear mapping of the two pulse rate measurements as a function of said reliability measures; and removing measurement noise and residual non-modelled contributions from said first and second enhanced signals using a noise reduction algorithm after subtracting said model from each of the first and second input signals ($y_1(t)$, $y_2(t)$).

20. Method according to claim 19, wherein said model is a nonlinear model.

21. Method according to claim 20, wherein said processing first and second input signals comprises selecting the model using a Minimum Description Length (MDL) criterion.

22. Method according to claim 20, wherein said nonlinear model is a third order polynomial moving average model.

23. Method according to claim 19, wherein said noise reduction algorithm is based on Principal Component Analysis (PCA).

* * * * *